United States Patent [19]

Rothrum et al.

[11] Patent Number: 5,593,750

[45] Date of Patent: Jan. 14, 1997

[54] CLOTH BODY COVERINGS HAVING MULTI-CYCLE REFASTENABLE TAPE CLOSURE SYSTEMS

[75] Inventors: Robert J. Rothrum, Coon Rapids; Linda C. Chaffee, Little Canada; Kelly T. McGurran, North Oaks, all of Minn.

[73] Assignee: Minnesota Mining and Manufacturing Company, St. Paul, Minn.

[21] Appl. No.: 460,306

[22] Filed: Jun. 2, 1995

Related U.S. Application Data

[62] Division of Ser. No. 320,106, Oct. 6, 1994, which is a continuation of Ser. No. 58,439, May 7, 1993, abandoned, which is a continuation-in-part of Ser. No. 788,255, Nov. 5, 1991, abandoned.

[51] Int. Cl.$^6$ .............................. A61F 13/56; B32B 3/02
[52] U.S. Cl. .................... 428/40.1; 428/131; 428/136; 428/137; 428/138; 428/192; 428/194; 428/195; 428/212; 428/354; 428/355; 604/385.1; 604/385.2; 604/389; 604/390
[58] Field of Search ............... 428/40, 41, 192, 428/193, 354, 355, 194, 195, 131, 136, 137, 138, 212; 604/389, 390, 385.1, 385.2

[56] References Cited

U.S. PATENT DOCUMENTS

| | | | |
|---|---|---|---|
| Re. 24,906 | 12/1960 | Ulrich | 206/59 |
| 2,109,583 | 3/1938 | Bennett | 154/43 |
| 2,532,011 | 11/1950 | Dahlquist et al. | 154/53.5 |
| 2,607,711 | 8/1952 | Hendricks | 117/122 |
| 3,168,749 | 2/1965 | Cala | 2/243 |
| 3,188,265 | 6/1965 | Charbonneau | 161/188 |
| 3,188,266 | 6/1965 | Charbonneau et al. | 161/188 |
| 3,318,852 | 5/1967 | Dixon | 260/78.5 |
| 3,389,827 | 6/1968 | Abere et al. | 220/53 |
| 3,451,062 | 6/1969 | Bradley | 2/114 |
| 3,503,568 | 3/1970 | Galley | 242/74 |
| 3,570,012 | 3/1971 | Winters | 2/114 |
| 3,848,596 | 11/1974 | Pennau | 604/390 |
| 3,871,369 | 3/1975 | Krzewinski | 128/132 |
| 4,000,521 | 1/1977 | Zoephel et al. | 2/114 |
| 4,034,752 | 7/1977 | Tritsch | 128/184 |
| 4,043,340 | 8/1977 | Cepuritis | 128/287 |
| 4,418,105 | 11/1983 | Stratton | 428/40 |
| 4,471,769 | 9/1984 | Lockhart | 128/132 |
| 4,522,853 | 6/1985 | Szonn et al. | 428/40 |
| 4,643,730 | 2/1987 | Chen et al. | 604/390 |
| 4,710,190 | 12/1987 | Wood et al. | 604/389 |
| 4,769,024 | 9/1988 | Pike et al. | 604/390 |
| 4,795,456 | 1/1989 | Borgers | 604/389 |
| 4,801,480 | 1/1989 | Panza et al. | 428/40 |
| 4,850,992 | 7/1989 | Amaral et al. | 604/389 |

(List continued on next page.)

FOREIGN PATENT DOCUMENTS

| | | |
|---|---|---|
| 0426359 | 5/1991 | European Pat. Off. . |
| 4010567A1 | 10/1991 | Germany . |
| 2148095 | 5/1985 | United Kingdom . |

OTHER PUBLICATIONS

Patent Abstracts of Japan vol. 14, No.275 for JP2082974.

*Primary Examiner*—Nasser Ahmad
*Attorney, Agent, or Firm*—Gary L. Griswold; Walter N. Kirn; John H. Hornickel

[57] ABSTRACT

A multi-cycle refastenable tape closure system is disclosed. The tape closure system comprises a fastener tape component having double-coated surfaces of pressure sensitive adhesive having the same or substantially similar pressure sensitive adhesive properties and preferably also a release tape component having opposing surfaces of pressure sensitive adhesive and a low adhesion release layer. The fastener tape component and the release tape component are capable of firmly adhering to opposing body coverings or along opposing edges of one body covering and capable of releasably adhering to each other to provide a multi-cycle refastenable contact of opposing body coverings or closure of the body covering opposing seams in an overlapping, low profile manner. A method of using a multi-cycle refastenable tape closure system is also disclosed.

17 Claims, 1 Drawing Sheet

U.S. PATENT DOCUMENTS

| | | | |
|---|---|---|---|
| 4,861,635 | 8/1989 | Carpenter et al. | 428/40 |
| 4,959,265 | 9/1990 | Wood et al. | 428/343 |
| 4,969,215 | 11/1990 | Burkett | 2/114 |
| 4,985,025 | 1/1991 | Lingertat et al. | 604/390 |
| 5,019,071 | 5/1991 | Bany et al. | 604/389 |
| 5,071,415 | 12/1991 | Takemoto | 604/389 |
| 5,158,557 | 10/1992 | Noreen | 604/389 |
| 5,462,540 | 10/1995 | Caldwell | 604/389 |

CLOTH BODY COVERINGS HAVING MULTI-CYCLE REFASTENABLE TAPE CLOSURE SYSTEMS

This is a division of application Ser. No. 08/320,106, filed Oct. 6, 1994.

FIELD OF THE INVENTION

This invention relates to multi-cycle refastenable pressure-sensitive adhesive tape closure systems, methods of use, and articles incorporating such tape closure systems thereon.

BACKGROUND OF THE INVENTION

Coverings have been used to protect and otherwise serve mammalian bodies for centuries. Body coverings have been constructed with portions thereof requiring closure. A myriad of fastening devices have been employed to permit opening and closing of body coverings. Among these include drawstrings, snaps, hook-and-loop fastening systems, pins, buttons, and the like. Ease and multiple cycling of various refastenable systems varies according to integrity of seams surrounding such closures, integrity of a fastening means, and manual dexterity required for fastening and unfastening through multiple cycles. For example, use of buttons or drawstrings on a hospital gown for a human patient requires considerable manual dexterity with often unacceptable and uncomfortable results.

Body coverings are integral or multi-component materials and can include without limitation garments, medical drapes, medical gowns, medical smocks, footwear coverings, ostomy appliances, incontinence products, diapers, feminine hygiene products, industrial clean room garments, tube or tool fixation restraints, body transfer sheets, fluid or exudate collection pouches, and other components, (such as splints or arm boards), capable of being joined together or with other components to function in close proximity with at least a portion of a mammalian body.

In recent years, disposable body coverings have become increasingly popular. Among disposable body coverings enjoying considerable popularity are disposable children's diapers. Refastenable pressure sensitive adhesive tape closure systems have become common in use with disposable children's diapers where back and front sections of a diaper are closed in a refastenable manner. Single-coated pressure sensitive adhesive tape tabs on the back portion of the diaper are releasably fastened to a release strip resident on the back portion of the diaper using the single-coated adhesive surface. These tabs are unpeeled and applied in a releasable fashion using the single-coated adhesive surface to a release surface on the front portion of the diaper. The same single coating of pressure sensitive adhesive both releases from the back portion of the diaper and adheres to the front portion of the diaper. Such tabs strategically placed on the front portion of the diaper create a snug-fitting diaper where portions of the back of the diaper overlap portions of the front of the diaper. Because such tabs have a single coating of adhesive, such tabs adhere in a position extending from the point of overlap of the back portion of the diaper to the front portion of the diaper. Thus, the tabs remain exposed to possible disruption and disconnection.

Representative examples of such single-coated tape disposable diaper closure systems are found in U.S. Pat. No. 4,710,190 (Wood et al.), U.S. Pat. No. 4,861,635 (Carpenter et al.), U.S. Pat. No. 4,801,480 (Panza et al.), and U.S. Pat. No. 5,019,071 (Bany et al). A double-coated tape, for use with undergarments, having an array of bluntly pointed stems protruding beyond the pressure sensitive adhesive layer contacting the undergarment is disclosed in U.S. Pat. No. 4,959,265 (Wood et al) .

SUMMARY OF THE INVENTION

The present invention solves the need for a fastening system for overlapping body coverings or overlapping edges of one body covering by providing a multi-cycle refastenable pressure sensitive adhesive tape closure system which can provide uninterrupted, continuous seal protection at locations of overlapping body coverings or overlapping edges of one body covering. The refastenable tape closure system of the present invention employs in one embodiment a combination of pressure sensitive adhesive tapes which, when fastened, provide sufficient shear strength to minimize unintended disconnection yet provides peel adhesion which can be a minimum sufficient to permit facile reopening of body coverings with minimal manual dexterity required.

A multi-cycle refastenable tape closure system of the present invention comprises in one embodiment a fastener tape component. In another embodiment, a multi-cycle refastenable tape closure system comprises both a fastener tape component and a release tape component.

The fastener tape component comprises a field of a first pressure sensitive adhesive coated on a first surface of a first backing and a field of a second pressure sensitive adhesive coated on a second and opposite surface of the first backing.

Another embodiment of a fastener tape component comprises a field of a first pressure sensitive adhesive coated on a first surface of a first backing and a field of second pressure sensitive adhesive coated on a second backing which is adhesively laminated to a second surface of the first backing.

In both embodiments of a fastener tape component, the first pressure sensitive adhesive is capable of firmly adhering along a first edge of a body covering and second pressure sensitive adhesive field is capable of releasably adhering to a second body covering or along a second edge of the body covering opposing the first edge of the body covering in a multi-cycle, refastenable manner to contact opposing body coverings or to close the opposing first and second edges of the body covering to form an overlapping, low profile seam which has a high dynamic shear force against unintended reopening but a low peel force for intended reopening in the axis of the seam.

Preferably, the first pressure sensitive adhesive field has a higher tack based on larger unit area and optionally a heavier coating weight than the second pressure sensitive adhesive field. "Higher tack" refers to the surface adhesiveness due to amount of surface coverage and optionally coating weight notwithstanding the fact that the two fields have the same or similar adhesive formulation. Thus, there is a differential adhesiveness ratio based on amount of surface exposed. For ease of manufacturing and use, the pressure sensitive adhesive of the first field has the same or substantially similar adhesive properties as the pressure sensitive adhesive of the second field. "Same or substantially similar adhesive properties" means the formulations chosen for adhesives are not substantially distinguishable in adhesive properties but need not be the same formulation. Further, the second pressure sensitive adhesive field occupies less than the entire surface of the fastener tape component on which the second pressure sensitive adhesive field is coated during an intended use. During a finite multiple cycles of reuse, one embodiment of the invention can provide the second pressure sensitive adhesive field with multiple-segmented release liners covering portions of the second pressure sensitive adhesive field. Alternatively, the second pressure sensitive adhesive field is bordered by non-adhesive zones of such surface.

The release tape component comprises a backing having first and second opposing surfaces with the first surface of the release tape component covered with a low adhesion release layer and the second surface of the release tape component coated with a field of a third pressure sensitive adhesive. The third pressure sensitive adhesive field is capable of firmly adhering to the second body covering or along an opposing edge of the first body covering and the second pressure sensitive adhesive field of the fastener tape component is capable of adhering to the low adhesion release layer in a multi-cycle, refastenable manner to contact opposing body coverings or to close the opposing edges of the body covering to form an overlapping, low profile seam.

The present invention includes a method of using a multi-cycle refastenable tape closure system of the present invention. The method comprises applying a fastener tape component described above along at least one edge of a first body covering and closing the edge over an opposing body covering or an opposing edge of the first body covering in an overlapping manner to form a low profile seam.

The present invention also includes a body covering comprising a natural or synthetic material having at least one edge capable of forming a seam, and a fastener tape component described above, with the first pressure sensitive adhesive field adhered along the edge of the body covering.

A feature of the present invention is the multi-cycle refastenable tape closure system utilizes a double-coated pressure sensitive adhesive tape or combination of double coated and single coated pressure sensitive adhesive tapes as a fastener tape component and a single-coated tape having a low adhesion opposing surface as the release tape component. Preferably, the multi-cycle refastenable tape closure system utilizes a double-coated pressure sensitive adhesive tape.

It is another feature of the present invention that conventional and commercially available double-coated tapes can be employed as the fastener tape component and conventional, commercially available single-coated tapes having a low adhesion opposing surface can be employed as the release tape component. The multi-cycle refastenable tape closure system of the present invention can employ commercially available materials in an unexpected combination to provide a low profile refastening of opposing body covering or opposing edges of one body covering in an overlapping manner.

It is another feature of the present invention that opposing pressure sensitive adhesive surfaces of fastener tape components have the same or substantially similar adhesive properties per unit area and differing coverages of opposing surfaces of such fastener tape component.

It is another feature of the present invention that the adhesive surface of the fastener tape component adhering to the low adhesion release layer of the release tape component can provide a seal for opposing body covering or opposing edges of one body covering in an overlapping manner to minimize leakage of materials therethrough in either direction. This feature is important for infection control in medical uses or for contaminants in industrial applications.

It is another feature of the present invention that multi-cycle refastenable tape closure systems of the present invention are covered by overlapping edges of the body covering when closed, minimizing unintended disconnection of the closed body covering.

It is another feature of the present invention that the first pressure sensitive adhesive field contacting one seam of the body covering has a higher peel force than the peel force of the adhesion of the second pressure sensitive adhesive field to the low adhesion release layer.

It is another feature of the present invention that the tape closure system can have a higher dynamic shear strength than the body covering to which the tape closure system is adhered.

It is another feature of the present invention that the low adhesion surface of the release tape component is wider than the pressure sensitive adhesive surface of the fastener tape component, such that all of the second pressure sensitive adhesive field on the fastener tape component can releasably adhere to the low adhesion release layer on the release tape component when opposing body coverings or opposing edges of one body covering overlap.

It is another feature of the present invention that the tape closure system remains functional after exposure up to at least 50 kGys, a dosage often used for sterilization of medical devices.

It is another feature of the present invention for an embodiment of the present invention to provide a double coated tape having a multiple slit release liner covering the second field of pressure sensitive adhesive as the fastener tape component, permitting the option of exposing one or more segments of the second field to provide differing amounts of adhesive exposure while providing differing coverages of the first field of pressure sensitive adhesive relative to the second field of pressure sensitive adhesive.

It is an advantage of the present invention that the tape closure system is refastenable in a multi-cycle fashion permitting opposing body coverings or opposing edges of one body covering to repeatedly overlap and close in a low profile manner minimizing discomfort from fastening of such opposing items.

It is another advantage of the present invention that multi-cycle refastenable tape closure systems of the present invention can be employed during diagnostic or therapeutic medical procedures where repeated access to portions of the human body are required at a variety of intervals, while permitting comfort and modesty when access to such body locations is not required.

It is another advantage of the present invention that multi-cycle refastenable tape closure system of the present invention employ fastener tape components and release tape components which, when peeled apart, make a distinctive tearing sound. This distinctive sound can also provide audible indication of either intended or unintended opening of overlapping edges of the body covering.

Embodiments of the invention are described in relation to the Drawing.

EMBODIMENTS OF THE INVENTION

A multi-cycle refastenable tape closure system of the present invention comprises at least a fastener tape component having pressure sensitive adhesive coated surfaces, preferably having the same or substantially similar adhesive properties and also having differing surface areas of adhesive fields exposed to contact with a cloth body covering. A fastener tape component can firmly adhere along one edge of a body covering and releasably adhere to a second body covering or along an opposing edge of the first body covering or preferably to a release tape component. Both fastener tape component and release tape component can be provided as strips of material for firmly adhering along opposing body coverings or opposing edges of one body covering within such edges intended for providing the overlap of the body covering seam. Thus, the refastenable tape closure system is within the overlapping seam and not exposed to unintended disruption by protruding from the overlapping seam.

Figure 1:
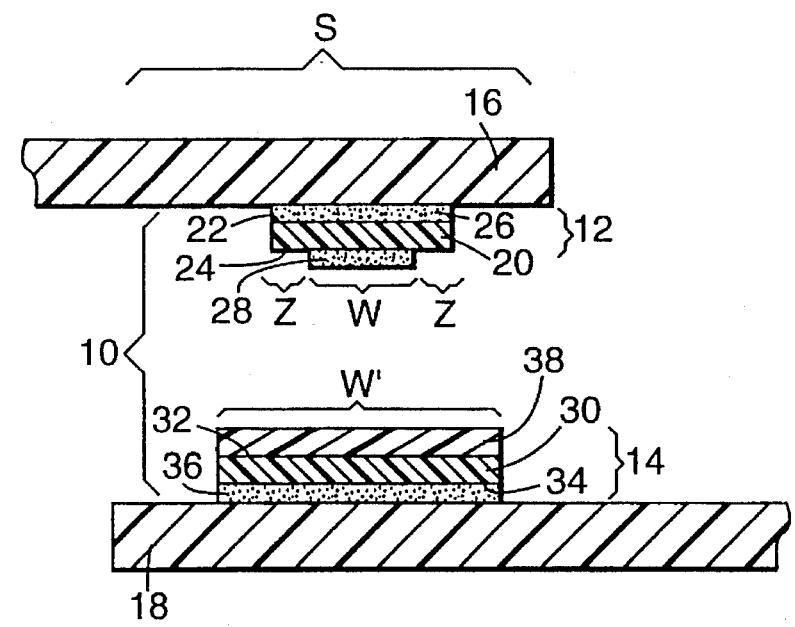
FIG. 1 is a cross-sectional view of a multi-cycle refastenable tape closure system of the present invention employed between overlapping edges of a body covering.

FIG. 1 shows an embodiment where opposing edges of one body covering are to be closed. Multi-cycle refastenable tape closure system, generally referred to as 10, comprises a fastener tape component 12 and a release tape component 14. Fastener tape component 12 is adhered along an inside surface of an outer body covering edge 16 while release tape component 14 is adhered along an outside surface of an inner body covering edge 18. The letter, S, indicates the extent of overlap of edges 16 and 18 within which tape closure system 10 is adhered for fastening and unfastening such edges 16 and 18 over multiple cycles.

Fastener tape component 12 comprises a backing 20 having opposing surfaces 22 and 24. A field 26 of first or covering pressure sensitive adhesive is coated on surface 22 and available for firm adhesion along outer body covering edge 16. Field 28 of second or fastening adhesive is coated on and preferably centered on surface 24 and available for releasable adhesion to the release tape component 14 or edge 18.

Release tape component 14 comprises a backing 30 having opposing surfaces 32 and 34. A field 36 of third or covering pressure sensitive adhesive is coated on surface 34 and available for firm adhesion along inner body covering edge 18. A low adhesion layer 38, such as a low adhesion "backsize" material is coated on or otherwise comprising surface 32.

While in the embodiment shown in FIG. 1, fastener tape component 12 is adhered along the edge 16 which overlaps and release tape component 14 is adhered along the edge 18 which is overlapped, that arrangement of components 12 and 14 can be reversed to provide component 12 on the overlapped edge 18 and component 14 on the overlapping edge 16.

Fastener Tape Component

As seen in FIG. 1, adhesive 28 can cover at least a portion of surface 24 and preferably need not cover the entire surface 24. Most preferably, for control of releasable adhesion, adhesive 28 occupies a center portion of surface 24 with zones, Z, of non-adhesive area bordering adhesive 28. Provision of zones, Z, minimizes possible contact of adhesive 28 with edge 16, which further minimizes lifting of component 12 from edge 16 when adhesive 28 releases from edge 18 or layer 38.

By comparison, low adhesion release layer 38 of release tape component 14 can cover the entire surface 32 of release backing 30. Preferably, fastening width, W, is a smaller dimension than release width, W', thereby maximizing the area on low adhesion release layer 38 on which fastening adhesive 28 can releasably adhere for sealing of edges 16 and 18 at overlap, S, into a low profile seam.

As shown in FIG. 1, covering adhesive 26 can be wider than fastening width W for fastening adhesive 28. Preferably, the ratio of adhesive 26 width to adhesive 28 width is about 2 to 1. These relative dimensions are preferred when covering adhesive 26 and fastening adhesive 28 comprise the same or similar pressure sensitive adhesive formulations having the same or similar tack per unit area. Thus, covering adhesive 26 and fastening adhesive 28 have the same or substantially similar adhesive properties. Preferably, these substantially similar adhesive properties for adhesive fields 26 and 28 are achieved by employing the same or substantial related pressure sensitive adhesive formulations for both adhesive fields 26 and 28. Most preferably, for ease of manufacturing and application of the fastener tape component 12, the same pressure sensitive adhesive is selected for both adhesive fields 26 and 28. Thus, it is the differential of the exposed adhesive surfaces between fields 26 and 28, not the type of adhesives having the same or substantially similar adhesive properties that are employed, that provides the firm adhesion for field 26 and the releasable adhesion for field 28. Preferably, the differing exposed adhesive surfaces has a ratio of adhesive 26 width to adhesive 28 width is about 2 to 1, as described above.

Thus, it is presently preferred that greater adhesion occur between covering adhesive 26 and outer body covering edge 16 as compared with the adhesion of fastening adhesive 28 with low adhesion release layer 38 of release tape component 14. Preferably, covering adhesive 26 has the same or substantially similar pressure sensitive adhesive properties, such as tack, as fastening adhesive 28. For example, using the same pressure sensitive adhesive or related pressure sensitive adhesives having the same or substantially similar pressure sensitive adhesive properties as both covering adhesive 26 and fastening adhesive 28, surfaces 22 and 24 can have a differential adhesiveness ratio of surface 22:surface 24 of from about 1.1:1 to about 1.9:1 and preferably about 1.6:1.

Fastener tape component 12 can employ commercially available medical tapes. In those instances, covering adhesive 26 and fastening adhesive 28 are typically of the same or similar width. Non-limiting examples of acceptable fastening tape components 12 include No. 1509 transparent polyethylene 0.124 mm double-coated medical tape; No. 1512 transparent polyethylene 0.086 mm double-coated medical tape; No. 1513 transparent polyester 0.086 mm double-coated medical tape; No. 1522 transparent polyethylene 0.160 mm double-coated medical tape; No. 9874 transparent polyethylene 0.122 mm double-coated medical tape; No. 9920 0.024 mm double-coated polyethylene fastener tape; No. 9877 0.114 mm double-coated polyester high performance tape; and No. 9878 water disperable adhesive tape 0.1 mm double-coated medical tape. All of the above-identified commercially available tapes, (except No. 9877 tape which is a Kraton based medical tape), consist of the appropriate backing coated on both sides with a hypoallergenic, pressure sensitive acrylate adhesive wound with a silicone treated bleached Kraft-Glassine paper liner for adhesive protection. All of the above-identified commercially available tapes are available from Minnesota Mining and Manufacturing Company of St. Paul, Minn., U.S.A. Most of these medical tapes are identified in *3M Medical Specialties Product Reference Guide* published by 3M Health Care in 1991 and available from 3M Medical Specialties Department, the disclosure of which is incorporated by reference herein. The remainder of these medical tapes are also available in publications from 3M Medical Specialties Department.

Alternatively, other commercially available tapes are useful. One example is No. 9416 tape commercially available from Minnesota Mining and Manufacturing Company. It is a double coated tape of two different pressure sensitive adhesives having different coating masses flood coated on opposing surfaces of a backing.

Figure 2:
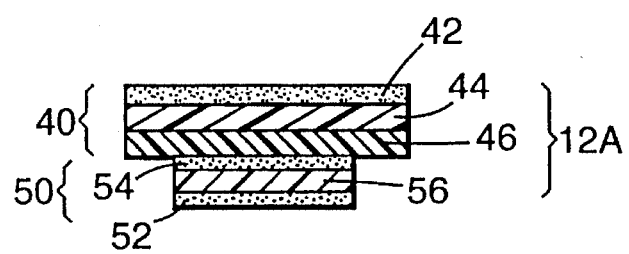
FIG. 2 is a cross-sectional view of an alternate embodiment of a fastener tape component useful in a multi-cycle refastenable tape closure system of the present invention.

Alternatively, as seen in FIG. 2, fastener tape component 12A can comprise a laminate of a double coated pressure sensitive adhesive tape of one width to a single coated pressure sensitive adhesive tape of a greater width.

The single coated tape can serve as an anchoring tape 40 having a field 42 of relatively higher tack pressure sensitive adhesive coated on a first side of backing 44. Backing 44 has a non-adhesive surface or layer 46 on a second side opposing the first side. Preferably, surface or layer 46 has a microstructured surface, a matte finish, or a corona treatment to improve receptivity to adhesion.

The double coated tape can serve as a fastening tape 50 having fields 52 and 54 of relatively lower tack pressure sensitive adhesive coated on opposing sides of a backing 56. Preferably, field 54 firmly adheres to surface 46 along a central portion of surface 46, leaving zones of non-adhesive surfaces in the same manner and for the same reasons as described with respect to component 12 in FIG. 1. Further, the fields 42 and 52 can use pressure sensitive adhesives having the same or substantially similar adhesive properties for the same reasons as described for component 12 in FIG. 1.

Figure 3:
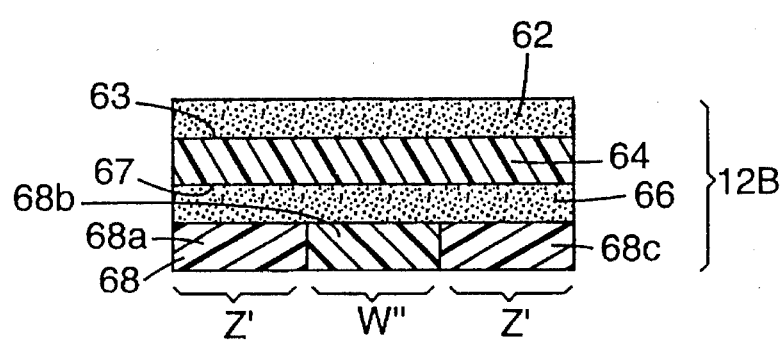
FIG. 3 is a cross-sectional view of an alternate embodiment of a fastener tape component useful in a finite number of multiple refastenings.

Alternatively as seen in FIG. 3, fastener tape component 12B shows an embodiment where field 62 of pressure sensitive adhesive coats one surface 63 of backing 64 and field 66 of a pressure sensitive adhesive, having the same or substantially similar pressure sensitive adhesive properties as the adhesive of field 62, coats the opposing surface 67. Component 12B differs from component 12 in that field 66 covers substantially the same area of surface 67 as field 62 covers surface 63. Further, field 66 is covered by a multiple-segmented release liner 68, shown in the example of FIG. 3 to be in three segments 68a, 68b, and 68c with segments 68a and 68c having a width Z' corresponding to width Z seen in FIG. 1 and with width W" corresponding to width W seen in FIG. 1.

Removal of any single segment of liner 68, for example segment 68b, exposes field 66 in a surface area to provide a pressure sensitive adhesive surface of width W" in a similar ratio as that seen in FIG. 1 because release liner segments 68a and 68c keep the remainder of field 66 unexposed to releaseably contact to body coverings.

Moreover, sequential releasing of release liner segment 68a or 68c will expose increasing surface areas of field 66 such that the differential adhesiveness ratio for surface 63:surface 67 approaches 1:1.

Alternatively, if field 66 exposed by release liner segment 68b becomes soiled or used such that its adhesiveness is spent, a second segment of release liner 68 can then be removed to expose a virgin portion of field 66 for a second cycle of usage. The number of cycles is determined by the number of segments of liner 68. Preferably, the segments are of even width but can be of uneven width for controlling the manner of adhesiveness and order of adhesive re-fastenings. For example, if used on a surgical gown for fastening of the collar prior a surgeon entering a surgical arena, a smaller segmented release liner could be removed for preliminary placement of the overlapping collar to determine comfortable fit followed by removal of a larger segmented release liner to provide more secure collar fastening. In that instance as few as two or three segments in liner 68 need to be employed.

Like component 12, component 12B provides a flat, flexible fastening tape component for use in a multi-cycle refastenable tape closure system that can operate in a finite number of multiple refastenings.

Commercially available single coated medical tapes are acceptable for use as anchoring tape 40. Nonlimiting examples are No. 1523 tan 0.13 mm polyethylene medical tape; No. 1526 transparent 0.13 mm polyethylene medical tape; No. 9830 transparent 0.07 mm polyethylene medical tape; and No. 9835 white 0.14 mm coextruded ethylene vinyl acetate/polyethylene medical tape. Nos. 1523, 1526, and 9830 medical tapes have matte finishes on the non-adhesive surface. Nos. 1523 and 1526 medical tapes have matte finished, non-adhesive surfaces which are corona treated. All of the tapes are coated on one surface with a hypoallergenic, pressure sensitive acrylate adhesive. All of the tapes are wound with a bleached Kraft paper liner having a silicone-treated, polyethylene coated surface. All of the enumerated medical tapes are commercially available from Minnesota Mining and Manufacturing Company.

Commercially available double coated medical tapes described with respect to fastener tape component 12 can be employed as fastening tape 50.

Acceptable combination of tapes 40 and 50 can be laminated to form fastener tape component 12A. Nonlimiting examples are laminates of No. 1509 and No. 1526 medical tapes; No. 1509 and No. 1523 medical tapes; No. 1512 and No. 1526 medical tapes; and No. 1513 and No. 1526 medical tapes. Preferred is a combination of No. 1526 0.127 mm transparent polyethylene single-coated medical tape as anchoring tape 40 laminated to No. 1509 transparent polyethylene 0.124 mm double-coated medical tape as fastening tape 50.

Presently preferred for the fastening tape component 12 is a high-low tack double-coated medical tape having a coating mass of 11 grains/24 in$^2$ (about 4.6 mg/cm$^2$) for covering acrylate adhesive 26 flood coated on surface 22 of backing 20 and a coating weight of 7 grains/24 in$^2$ (2.9 mg/cm$^2$) for fastening acrylate adhesive 28 coated on a center zone portion of surface 24 of backing 20 now commercially available as No. 9920 0.024 mm double-coated polyethylene fastener tape.

Pressure sensitive acrylate adhesives suitable for either flood coating of surface 22 or zone coating of surface 24 can include copolymers which are reaction products of the polymerization of at least one A monomer and at least one B monomer to yield a copolymer having an inherent viscosity of about 1.0 dl/g to about 2.0 dl/g.

The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms.

The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof.

The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available.

The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer.

Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Adminstration recommends such evaluations in a Tripartite Biocompatibility Draft Guidance for Medical Devices. The commercially available medical tapes described above using acrylate pressure sensitive adhesives of the type described herein are considered hypoallergenic.

Presently preferred as an acrylate pressure sensitive adhesive for flood coating of surface 22 and zone coating of surface 24 is an isooctyl acrylate/acrylic acid copolymer in a weight ratio of about 94:6. The inherent viscosity of the copolymer is about 1.4–1.6 dl/g.

Preferably, acrylate pressure sensitive adhesives have a tackifier added to the formulation to improve tack. Commercially available tackifiers include "Foral" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

The presently preferred tackified adhesive is flood coated on surface 22 in a coating mass of about 4.6 mg/cm$^2$ (11 grains) and also zone coated in a center strip 1.27 cm wide on 2.54 cm wide surface 24 in a coating mass of about 2.9 mg/cm$^2$ (7 grains).

Alternate pressure sensitive adhesives useful in the present invention are hypoallergenic Kraton rubber-based pressure sensitive adhesives produced using styrene-butadiene or styrene-isoprene copolymers commercially available as Kraton branded copolymers from Shell Oil Company of Houston, Tex. A variety of Kraton based pressure sensitive adhesives are disclosed in U.S. Pats. No. 5,019,071 (Bany et al.) and U.S. Pat. No. 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as Escorez™ 1310LC branded tackifier commercially available from Exxon Chemicals, a solid C$_5$ tackifying resin commercially available as Wingtack™ Plus brand tackifier from Goodyear Tire and Rubber Company, Akron, Ohio and naphthenic oils having 10% aromatics commercially available as Shellflex™ 371 from Shell Oil Company. Such tackifiers can comprise about 45 to about 70 weight percent of the pressure sensitive adhesive, while the Kraton copolymer can comprise about 30 to 55 weight percent. Presently preferred is a Kraton based pressure sensitive adhesive comprising about 35 weight percent Kraton 1111, about 53 weight percent Wingtack Plus, about 11 weight percent Shellflex 371, and about 2 weight percent Irganox 1010 and 1076 branded antioxidants, in a similar formulation to that disclosed in Examples 1–13 of U.S. Pat. No. 5,019,071.

Pressure sensitive adhesive copolymers can be copolymerized using known polymerization techniques such as emulsion polymerization and solution polymerization. Sources of polymerization preparation and techniques include *Organic Polymer Chemistry,* Saunders et al. (Halsted Publishing Company, New York 1973); *Applied Polymer Science,* Tess et al. (American Chemical Society, Washington, D.C., 1981); *Principles of Polymerization,* Odien (John Wiley and Sons, New York, 1981); and the *Handbook of Pressure-Sensitive Adhesive Technology, Second Edition,* Satas, Ed., (Van Nostrand Reinhold Company, New York, 1989), the disclosures of which are incorporated by reference.

Specifically, acrylate pressure sensitive adhesive copolymers can be prepared according to U.S. Pat. No. 2,884,126/U.S. Pat. No. Re. 24,906 (Ulrich), the disclosure of which is incorporated by reference herein.

The presently preferred acrylate copolymer pressure sensitive adhesive can be prepared by emulsion polymerization according to Example 5 of U.S. Pat. No. 2,884,126/U.S. Pat. No. Re. 24,906, except that tackifier is added to the emulsion in an amount of about 35–40% weight percent of copolymer solids, and that tackified copolymer is dissolved in a heptane-isopropanol (70:30) solution.

The presently preferred Kraton copolymer pressure sensitive adhesive can be prepared in the manner as disclosed in Examples 1–13 of U.S. Pat. No. 5,019,071, the disclosure of which is incorporated by reference above.

Release Tape Component

Release tape components 14 can employ commercially available tapes. Non-limiting examples of such commercially available tapes include No. 1530 microporous rayon nonwoven medical tape having a width of 0.14 mm; No. 1530-L 0.14 mm microporous rayon nonwoven medical tape; No. 1516 clear 0.06 mm polyester medical tape; No. 910 repulpable tape dispersible in water; No. 9921-SL 0.058 mm polyester release tape and No. 9956 fluoropolymer 0.07 mm medical release liner laminated to No. 1509 transparent polyethylene 0.124 mm double-coated medical tape. Presently preferred for release tape component 14 is No. 9921-SL 0.058 mm polyester medical tape having a low adhesion backsize layer.

All of the above-identified commercially available tapes consist of the appropriate backing coated on one side with a hypoallergenic, pressure sensitive acrylate adhesive of the type described with respect to fastener tape component 12 or 12A above. No. 1509 medical tape also has a silicone treated, bleached Kraft-Glassine paper used as a release liner as the laminated 9956/1509 tape is wound on a roll. No. 1530-L medical tape also has a silicone treated, polyethylene coated bleached Kraft paper used as a release liner. Except for the laminated 9956/1509 tape, all of these tapes are commercially available from Minnesota Mining and Manufacturing Company. Both No. 9956 release liner and No. 1509 tape are individually commercially available.

Low adhesion release layer 38 is preferably a low adhesion backsize material which has been melt processed into or coated onto surface 32 of backing 30. Useful low adhesion backsize materials include polyolefins, cured silicones, polymethyl pentene, poly 1-octene, blends of silicones with polyethylene, blends of fluorochemicals with polypropylene, polyethylene, polyurethanes, or fluoro-chemicals grafted to polyolefins or similar polymers and the like. Particularly preferred low adhesion backsize materials are described in U.S. Pat. No. 2,532,011 (Dahlquist et al.) and include polyurethane coatings prepared from the grafted reaction product of 50% hydrolyzed polyvinyl acetate (36 weight percent) and octadecyl isocyanate (63 weight percent) and coated from a 5% solids mixture in toluene and xylene to become a very thin layer 38 on surface 32. Other low adhesion backsize materials are described in U.S. Pat. No. 2,607,711 (Hendricks) and U.S. Pat. No. 3,318,852. The preparation of low adhesion backsize materials is generally described, for example, in U.S. Pat. No. 2,532,011 (Dahlquist et al.), the disclosure of which is incorporated by reference herein.

Coating of low adhesion backsize materials to a backing in a manner to improve interface bonding of layer 38 to surface 32 of backing 30 can be accomplished according to methods disclosed in U.S. Pat. Nos. 3,188,265 and 3,188,266 (both Charbonneau et al.), the disclosures of which are incorporated by reference.

Body Coverings and Application of Tape Closure System

Body coverings can be constructed from natural or synthetic materials prepared in the form of films, membranes, nonwoven, woven, or other conventional constructions. Multi-cycle refastenable tape closure systems of the present invention are particularly suited for use with nonwoven fabrics employed as disposable garments and medical gowns.

Fastener tape component 12 and release tape component 14 can be dispensed as tapes wound with suitable protective liners on bulk rolls or multi-laminate bulk rolls. Liners can be slit cut for ease of removal. In the embodiment of FIG. 3, component 12B has release liner 68 slit cut in specific segments according to the description above. The tapes can be unwound, cut to suitable dimension, and applied to opposing body coverings or opposing edges of the applicable body covering requiring multi-cycle refastenable tape closure.

Properties of Tape Closure Systems

Peel force in a 90 "T-Peel" direction is used to determine the ease by which refastenable tape closure systems of the present invention can open closed seams of body coverings by a axial peeling of one edge 16 from the other edge 18. Peel force is measured in grams/0.5 inches and also reported in Newtons/meter (N/m).

Initial peel force (90°) of the fastener tape component 12 or 12A from the release tape component 14 can range from about 9 N/m to about 280 N/m, desirably from about 45 N/m to about 145 N/m, and preferably from about 70 N/m to about 100 N/m. Such peel force minimizes dexterity required for intended opening of opposing body coverings or opposing edges of one body covering when required.

Dynamic shear force is used to measure the strength of tape closure systems to resist unintended separation of a seam of the body covering by shear forces applied to the seam at an angle other than the axis of the seam. Dynamic shear force is measured in pounds/(0.5 inch machine direction)×(1.0 inch cross direction), also reported here in Newtons/meter$^2$ (N/m$^2$).

Dynamic shear strength of tape closure system 10 can range from about 50,000 N/m$^2$ to about 900,000 N/m$^2$, desirably from about 100,000 N/m$^2$ to about 200,000 N/m$^2$, and preferably from about 120,000 N/m$^2$ to about 170,000 N/m$^2$ in order to assure sealing of opposing body coverings or opposing edges of one body covering.

It is preferred that the peel force of covering adhesive 26, 42, or 62 from body covering edge 16 is greater than the peel force of fastening adhesive 28, 54, or that portion of field 66 exposed by removal of a segmented release liner 68 from low adhesion release layer 38. It is also presently preferred that tape closure system 10 has a higher dynamic shear strength than the body covering to which tape closure system 10 is adhered.

Further embodiments of the invention are found in the following examples.

EXAMPLES

EXAMPLES 1–6

In each of the Examples, 10 cm×12 cm pieces of No. 8818 spunlaced nonwoven fabric commercially available from E. I. DuPont de Nemours and Company of Wilmington, Del., U.S.A. were used with the release tape components and fastening tape components identified in Table 1. In each instance, subjective and qualitative testing of the multiple cycle refastenability of tape closure systems using the identified release tape components and fastening tape components resulted in meeting the objectives of adequate dynamic shear strength and peel force characteristics.

TABLE 1

| Example | Release Tape Component[1] | Fastener Tape Component[2] |
|---|---|---|
| 1 | No. 1530 nonwoven pressure sensitive adhesive (PSA) tape with low adhesion backsize | No. 1509 double-coated pressure sensitive medical tape |
| 2 | No. 1516 plastic PSA tape with low adhesion backsize | No. 1509 double-coated PSA medical tape |
| 3 | No. 9956 fluoropolymer release liner laminated to No. 1509 double-coated PSA medical tape | No. 1509 double-coated PSA medical tape |

[1]Commercially available from Minnesota Mining and Manufacturing Company, St. Paul, Minnesota, U.S.A.
[2]Commercially available from Minnesota Mining and Manufacturing Company, St. Paul, Minnesota, U.S.A.

EXAMPLES 4–8

Using a blue-colored spunlaced nonwoven fabric No. 8818 commercially available from DuPont of Wilmington, Del., refastenable tape closure systems of the present invention were measured for initial and repeat 90 T-Peel peel force and dynamic shear force according to the following procedures.

The release tape component employed was a 2.54 cm wide No. 1516 medical tape comprising a clear polyester backing having a single coating of pressure sensitive acrylate adhesive on one surface and a low-adhesion backsize on the other surface. The release tape component adhesive was firmly adhered to the "dark" side of the nonwoven fabric.

The fastener tape component was a laminate of a No. 1509 transparent polyethylene double-coated PSA medical tape 0.96 cm width, centered on a 2.54 cm width of No. 1526 transparent polyethylene single-coated PSA medical tape, which was firmly adhered to the "light" side of the nonwoven fabric.

EXAMPLE 4

A 2 kg roller was used to close the release tape component to the fastening tape component. Peel adhesion force of the fastening tape components from the release tape component was measured on an Instron 1122 tensile tester, 90° T-Peel at a 30 cm per minute rate with force measured in grams per 0.96 cm width and converted to N/m. In the first test, the open or unassembled fastener was closed and initial peel force was measured. After initial peel was measured, closure was repeated and remeasured 6 times. The test was replicated with six fastener tape closure system sets. The mean value of initial peel was 72 grams/0.96 cm (74 N/m) and the mean value for the recycle peel force was 57 grams/0.96 cm (59 N/m).

EXAMPLE 5

The test of Example 4 was repeated with six new sets having been aged in 90% relative humidity, 49° C. for 7 days. Initial peel force and repeated closure and peel force recycle six times for each of six sets was measured. Initial peel was a mean of 268 grams/0.96 cm (276 N/m) and reassembled fastener and repeat peel was a mean of 98 grams/0.96 cm (101 N/m).

EXAMPLE 6

This test repeated the first test of Example 4 except that each fastener set was irradiated with gamma cobalt-60 radiation at 50 kiloGrays prior to initial peel force and repeat closure peel force measurements. Initial peel force had a mean of 140 grams/0.96 cm (144 N/m) with reassembled and repeat peel force of having a mean of 75 grams/0.96 cm (77 N/m).

EXAMPLE 7

This test employed six tape closure system sets which were irradiated with gamma radiation from a cobalt-60 source at a dosage of 50 kiloGrays beginning with open or unassembled tape closure systems. A 2 kg roller was used to close a release type component to the fastener tape component of each closure system. The test of Example 6 was used. Initial peel force was measured having a mean of 45 grams/0.96 cm (46 N/m). After repeated closure and peel cycles of six repetitions for each tape closure system set, reassembled fastener and repeat peel force had a mean of 36 grams/0.96 cm (37 N/m).

EXAMPLE 8

Dynamic shear force of closed tape closure systems from Examples 4–7 was measured on a Instron 1122 tensile tester operating at 25.4 cm per minute. In each case, the nonwoven DuPont fabric failed prior to any failure of the closed tape closure system. Thus, the dynamic shear strength of the closed tape closure system was greater than the nonwoven fabric. Machine direction tensile strength of the nonwoven DuPont fabric was measured to be 12 pounds per inch (2102 N/m) at break. In each instance, the mode of failure was the nonwoven fabric and was unrelated to any delamination of either fastener tape component or release tape component delaminating from the nonwoven fabric. Thus, refastenable tape closure systems of the present invention peel open easily yet in a dynamic shear mode have exceptional strength.

EXAMPLES 9–13

Table 2 shows refastenable tape closure systems and substrates used to measure dynamic shear force.

TABLE 2

| Example | Release[1] | Fastening[1] | Substrate |
|---|---|---|---|
| 9 | No. 1516 | No. 1509/1526 | DuPont Blue Nonwoven[2] |
| 10 | No. 1516 | No. 1509/1526 | Stainless Steel |
| 11 | No. 1530-L | No. 1509/1526 | DuPont Blue Nonwoven |
| 12 | No. 910 | No. 9878 | DuPont Blue Nonwoven |
| 13 | No. 1516 | No. 9416 | DuPont Blue Nonwoven |

[1]Commercially available from Minnesota Mining and Manufacturing Company
[2]Commercially available from E. I. DuPont de Nemours of Wilmington, Delaware as No. 8818 spunlaced nonwoven fabric Testing was done on an Instron 1122 tensile tester with a crosshead speed set at 30 cm/min. A 2 kg roller was used to "close" the release tape and fastening tape components together and then tested immediately by clamping each set in the tester. Ten sets of each combination of Examples 11–13 were tested in a vertical axis of the tester. Dynamic shear force required to separate the closed system was measured in pounds/(0.5 inch machine direction)×(1.0 inch cross direction) and converted to N/m². In all sets of all Examples 9–13, the adhesive surface contact area was 1.27 cm machine direction by 2.54 cm cross direction. Results are shown in Table 3 below.

TABLE 3

| | Dynamic Shear Force | |
|---|---|---|
| Example | (pounds/(0.5 × 1)) | (N/m²) |
| 9 | 12.2 | 168,214 |
| 10 | 63.1 | 870,023 |
| 11 | 8.9 | 122,713 |
| 12 | 5.9 | 81,349 |
| 13 | 4.3 | 59,288 |

Peel force data for multiple samples of Examples 9, 11–13 were also tested on the Instron 1122 tensile tester with a crosshead speed set at 30 cm/min. A 2 kg roller was used to "close" the release tape component and fastening tape component of each system of Examples 9, 11–13 and tested for 90° T-Peel peel force to simulate unpeeling one edge of a garment from the other edge of the garment along the axis of overlap.

Initial peel force and repeat closure and peel cycle (6 repetitions) were done for each closure system and measured in grams/0.5 inch and converted to N/m. Table 4 shows the average of 10 sets of each system of Examples 9, 11–13.

TABLE 4

| Example | Initial gm/0.5 in (N/m) | Peel Force Repeat | | | | | |
|---|---|---|---|---|---|---|---|
| | | #1 | #2 | #3 | #4 | #5 | #6 |
| 9 | 105.7 (82) | 94.3 (73) | 93.5 (72) | 91.0 (70) | 89.5 (69) | 89.2 (69) | 88.7 (68) |
| 11 | 87.9 (68) | 89.9 (69) | 89.9 (69) | 90.0 (69) | 90.3 (70) | 91.7 (71) | 92.9 (72) |
| 12 | 16.4 (13) | 16.1 (12) | 15.8 (12) | 16.1 (12) | 15.8 (12) | 15.8 (12) | 15.5 (12) |
| 13 | 11.1 (9) | 10.2 (8) | 10.0 (8) | 9.9 (8) | 9.8 (8) | 9.8 (8) | 9.6 (7) |

Results from Table 4 show that the average of 10 sets of each combination of Examples 9, 11–13 are refastenable up to at least six closure cycles with consistent and low peel force values. Combined with high dynamic shear data shown in Table 3, each of the Examples 9, 11–13 demonstrates both high dynamic shear strength for strong closure against unintended opening and low peel adhesion for easy closing and intended reopening of the seam of a body garment fastened with a tape closure system of the present invention.

The invention is not limited to these embodiments. For an appreciation of the scope of the present invention, the claims follow.

What is claimed is:

1. A body covering, comprising:

(a) a natural or synthetic material having at least one edge capable of forming a seam; and (b) a fastener tape component and a release tape component;

said fastener tape component comprising:

(a) a first field of a first pressure sensitive adhesive coated on a first surface of a first backing and firmly adhered to a first edge of the body covering, and (b) a second field of a second pressure sensitive adhesive, the second pressure sensitive adhesive having the same or substantially similar pressure sensitive adhesive formulations as the first pressure sensitive adhesive, coated on a second surface of said first backing or coated on a second backing adhesively laminated to said second surface of said first backing and releasably adhered to a second body covering or along a second edge of the body covering opposing the first edge of the first body covering;

wherein surface area of said first pressure sensitive adhesive field adhered to the first edge of the body covering is larger than surface area of said second pressure sensitive adhesive field releasably adhered to the second body covering or the second edge of the body covering;

said release tape component comprising a backing having first and second opposing surfaces, said first surface of said release tape component covered with a low adhesion release layer, said second surface of said release tape component coated with a field of a third pressure sensitive adhesive, said third pressure sensitive adhesive field capable of firmly adhering to the second body covering or along the second edge of the first body covering opposing the first edge of the body covering, and said second pressure sensitive adhesive field capable of adhering to said low adhesion release layer in a multi-cycle, refastenable manner to contact opposing body coverings or to close the opposing edges of the body covering to form an overlapping, low profile seam, wherein said low adhesion release layer of release tape component is wider than said second field of pressure sensitive adhesive of said fastener tape component, such that all of said second field of pressure sensitive adhesive can releasably adhere to said low adhesion release layer when opposing body coverings or opposing edges of one body covering overlap, and wherein said second field of pressure sensitive adhesive occupies a center zone along said fastener tape component and non-adhesive zones border said center zone.

2. The body covering according to claim 1, wherein said body covering is a garment, medical drape, medical gown, medical smock, footwear covering, ostomy appliance, incontinence product, diaper, feminine hygiene product, splint, arm board, tube or tool restraint, body transfer sheet, fluid or exudate collection pouch, or industrial clean room garment.

3. The body covering according to claim 1, wherein said third field of pressure sensitive adhesive is firmly adhered to a second body covering or an along an opposing edge of the first body covering, and wherein said second field of pressure sensitive adhesive is capable of adhering to said low adhesion release layer in a manner that said opposing body coverings or said opposing edges of one body covering overlap and seal to form a low profile seam.

4. The body covering according to claim 3, wherein said body covering is a garment, medical drape, medical gown, medical smock, footwear covering, ostomy appliance, incontinence product, diaper, feminine hygiene product, splint, arm board, tube or tool restraint, body transfer sheet, fluid or exudate collection pouch, or industrial clean room garment.

5. The body covering according to claim 1, wherein said first pressure sensitive adhesive comprising said first field and said second pressure sensitive adhesive comprising said second field have the same pressure sensitive adhesive formulation.

6. The body covering according to claim 1, wherein tack for said first surface provided by said first field of pressure sensitive adhesive is higher than tack for said second surface provided by said second field of pressure sensitive adhesive.

7. The body covering according to claim 6, wherein said first pressure sensitive adhesive and said second pressure sensitive adhesive comprise the same formulation of pressure sensitive adhesive, wherein said formulation is selected from the group consisting of acrylate pressure sensitive adhesives and styrene copolymer pressure sensitive adhesives.

8. The body covering according to claim 1, wherein tack for said first surface provided by said first field of pressure sensitive adhesive is higher than tack for said second surface provided by said second field of pressure sensitive adhesive.

9. The body covering according to claim 1, wherein said first field of pressure sensitive adhesive has a higher peel force from the body covering than a peel force of said second field of pressure sensitive adhesive from said low adhesion release layer.

10. The body covering according to claim 1, wherein the tape closure system has a higher dynamic-shear strength than the body covering to which the tape closure system is adhered.

11. The body covering according to claim 1, wherein said second field of pressure sensitive adhesive peel force from said low adhesion release layer ranges after initial fastening from about 9 to about 280 Newtons/meter.

12. The body covering according to claim 11, wherein the tape closure system has a dynamic shear strength ranging from about 50,000 N/m$^2$ to about 900,000 N/m$^2$ and wherein said second field of pressure sensitive adhesive peel force from said low adhesion release layer ranges after about 6 cycles of refastening from about 7 to about 100 Newtons/meter.

13. The body covering according to claim 1, wherein said second field of pressure sensitive adhesive is protected by a multiple-segmented release liner.

14. The body covering according to claim 13, wherein said multiple-segmented release liner can be removed in at least one segment to expose, optionally sequentially, said second field of pressure sensitive adhesive for releasably adhering to the second body covering or along the second edge of the first body covering in a finite multi-cycle, refastenable manner.

15. The body covering according to claim 1, wherein the tape closure system remains functional after exposure to a sterilization dosage of up to at least 50 kGys.

16. The body covering according to claim 1, wherein said fastener component comprises a laminate of an anchoring tape and a fastening tape, said first pressure sensitive adhesive field coated on said anchoring tape, said second adhesive pressure sensitive adhesive field coated on said fastening tape, said anchoring tape and said fastening tape adhesively adhered by at least a fourth field of pressure sensitive adhesive.

17. The body covering according to claim 1, wherein said fastener component comprises a backing having opposing surfaces and said first field of pressure sensitive adhesive and said second field of pressure sensitive adhesive coated on said opposing surfaces.

* * * * *